US008795687B2

(12) United States Patent
Kojima et al.

(10) Patent No.: US 8,795,687 B2
(45) Date of Patent: Aug. 5, 2014

(54) WEST NILE VIRUS PRM-E SIGNAL PEPTIDE FACILITATING THE EFFICIENT ASSEMBLY, MATURATION, AND RELEASE OF VIRUS-LIKE PARTICLES (VLPS)

(75) Inventors: Asato Kojima, Tokyo (JP); Hidehiro Takahashi, Tokyo (JP); Toyokazu Ishikawa, Kagawa (JP)

(73) Assignees: Japan as Represented by the Director-General of National Institute of Infections Diseases, Tokyo (JP); The Research Foundation for Microbial Diseases of Osaka University, Suita (JP)

( * ) Notice: Subject to any disclaimer, the term of this patent is extended or adjusted under 35 U.S.C. 154(b) by 523 days.

(21) Appl. No.: 12/741,479

(22) PCT Filed: Nov. 7, 2008

(86) PCT No.: PCT/JP2008/070354
§ 371 (c)(1),
(2), (4) Date: Jun. 2, 2010

(87) PCT Pub. No.: WO2009/060961
PCT Pub. Date: May 14, 2009

(65) Prior Publication Data
US 2010/0247559 A1    Sep. 30, 2010

(30) Foreign Application Priority Data

Nov. 7, 2007  (JP) .................................. 2007-290169

(51) Int. Cl.
*A61K 39/12* (2006.01)
*A61K 38/00* (2006.01)

(52) U.S. Cl.
USPC ........................................ 424/218.1; 530/326

(58) Field of Classification Search
None
See application file for complete search history.

(56) References Cited

U.S. PATENT DOCUMENTS 6,733,994 B2 *   5/2004   Weiner et al. ................ 435/69.1
7,390,495 B2 *   6/2008   Despres et al. ............ 424/218.1

FOREIGN PATENT DOCUMENTS

| EP | 1 454 988 A1 * | 9/2004 |
| JP | 2004-065118 A | 3/2004 |
| WO | WO 01/60847 A2 | 8/2001 |
| WO | WO 02/28165 A2 | 4/2002 |
| WO | WO 2005/108560 A2 | 11/2005 |
| WO | WO 2007/103565 A2 | 9/2007 |

OTHER PUBLICATIONS

Lee, E., et al., Jan. 2000, Mutagenesis of the signal sequence of yellow fever virus prM protein: enhancement of signalase cleavage in vitro is lethal for virus production, J. Virol. 74(1):24-32.*

(Continued)

*Primary Examiner* — Jeffrey S. Parkin
(74) *Attorney, Agent, or Firm* — Leydig, Voit & Mayer, Ltd.

(57) ABSTRACT

The present invention provides virus-like particles (VLP) highly secreting or producing signal peptide obtained by altering a signal sequence derived from West Nile virus (WNV), the signal peptide, a WNV VLP secretion expression vector containing a nucleic acid encoding prM protein and E protein, a WNP VLP highly secreting or producing animal cell line harboring the vector, a WNV vaccine containing WNV VLP obtained by the cell line as an active ingredient, and a WNV DNA vaccine containing the VLP secretion expression vector as an active ingredient.

1 Claim, 8 Drawing Sheets

(56) References Cited

OTHER PUBLICATIONS

Lobigs, M., et al., A flavivirus signal peptide balances the catalytic activity of two proteases and thereby facilitates virus morphogenesis, Virol. 401:80-89.*
Robinson, A., et al., Jul. 1986, Isolation and properties of the signal region from ovalbumin, FEBS Letters 203(2):243-246.*
Cioffi, J. A., et al., Sep. 1989, Parallel effects of signal peptide hydrophobic core modifications on co-translational translocation and post-translational cleavage by purified signal peptidase, J. Biol. Chem. 264(25):15052-15058.*
Huang, C. Y.-H, et al., Jun. 2005, Chimeric dengue 2 PDK-53/West Nile NY99 viruses retain the phenotypic attenuation markers of the candidate PDK-53 vaccine virus and protect mice against lethal challenge with West Nile virus, J. Virol. 79(12):7300-7310.*

Kojima et al., *Journal of Virology*, 77(16): 8745-8755 (Aug. 2003).

Takahashi et al., *Microbes and Infection,* 11: 1019-1028 (2009).

Agrawal et al., *The Journal of Infectious Diseases,* 188: 1-4 (2003).

Borisevich et al., *Virology,* 349: 371-381 (2006).

Borisevich et al., "West Nile virus (lineage 1 strain NY99), complete genome," *Database GenBank* [Online], Accession No. (NCBI Reference Sequence) NC_009942 (Oct. 19, 2007) [retrieved from URL <http://www.ncbi.nlm.nih.gov/entrez/viewerfcgi?158516887:NCBI:19326278> (Nov. 21, 2008)].

Takahashi et al., *The Japanese Society of Virology* [*Gakujutsu Shukai Program Shorokushu*], 54: 241, Abstract 1P022 (Nov. 1, 2006).

European Patent Office, Supplementary European Search Report in European Patent Application No. 08846317 (Oct. 12, 2010).

Japanese Patent Office, International Search Report in International Patent Application No. PCT/JP2008/070354 (Dec. 2, 2008).

* cited by examiner

1   M-RSSKQKKRGGKT
 2     M-SSKQKKRGGKT
 3       M-SKQKKRGGKT
 4         M-KQKKRGGKT
 5           M-QKKRGGKT
 6             M-KKRGGKT
 7               M-KRGGKT
 8                 M-RGGKT
 9                   M-GGKT
10                     M-GKT
11                       M-KT
12                         M-T
13                           M-N
14                             M-S
```

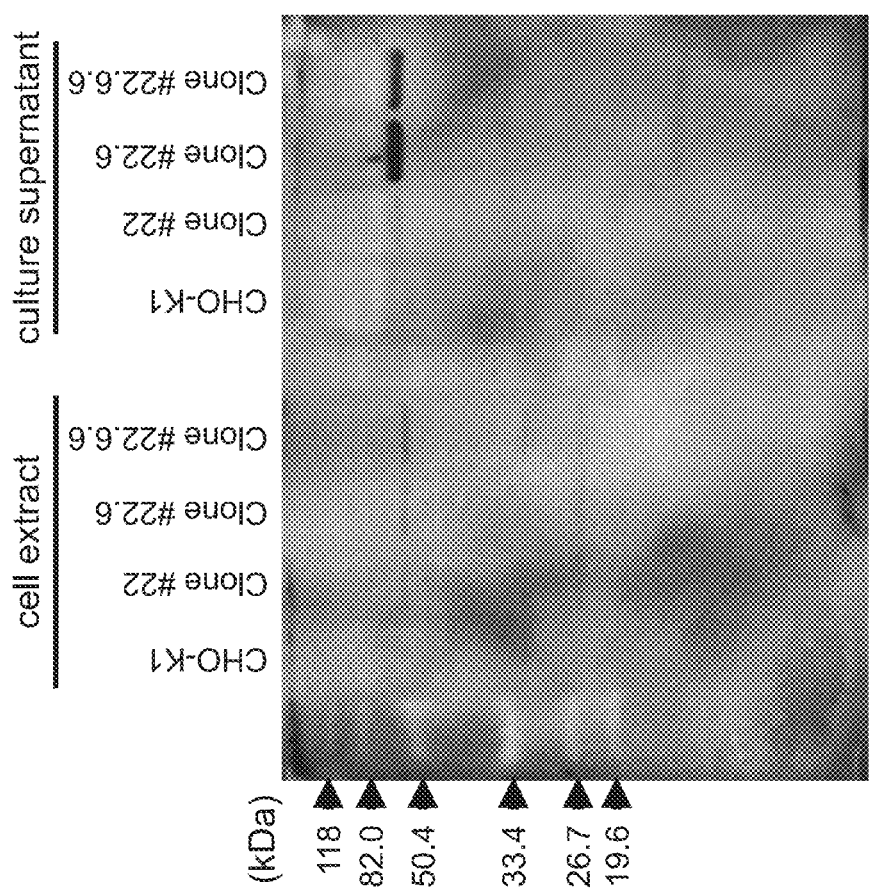

US 8,795,687 B2

WEST NILE VIRUS PRM-E SIGNAL PEPTIDE FACILITATING THE EFFICIENT ASSEMBLY, MATURATION, AND RELEASE OF VIRUS-LIKE PARTICLES (VLPS)

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 22,216 bytes ASCII (Text) file named "706392ReplacementSequenceListing" created Jan. 2, 2013.

TECHNICAL FIELD

The present invention relates to an artificial signal peptide enabling high secretion expression of virus-like particles of West Nile virus, a recombinant expression vector comprising a nucleic acid encoding a West Nile virus-derived protein including the signal peptide, a transformant harboring the vector, a production method of virus-like particles of West Nile virus by using the transformant, West Nile virus vaccine containing virus-like particles obtained by the method and the like.

BACKGROUND ART

West Nile fever is a systemic acute fever disease caused by infection with West Nile virus (WNV). Occasionally, the virus invades and grows in the central nervous system to cause lethal brain meningitis. WNV is widely distributed in Africa, Middle East, part of Europe, Russia, India, Indonesia and the like. The virus is maintained and propagated by an infection ring between *Culex* species as a vector and birds (wild and domestic) as an amplification animal. During the process, human, horse and domestic animals become accidental hosts.

In summer 1999, WNV invaded and was indigenized in New York, USA, and has continuously been expanding since then. It was confirmed that more than 2300 persons were infected by the end of September last year (2007) throughout the United States, thus causing a serious problem for the public health. A WNV vaccine for human does not exist in the world at present.

Under the circumstances, propagation of the virus to Asian countries including Japan has been feared, and practicalization of human vaccine has been desired. while culture Vero cell-derived virus inactivation vaccines are being urgently developed at present, there is an increasing need for the development of a subunit vaccine that can be produced safely at a low cost without using a biosafety level 3 virus in the production step.

WNV was first isolated in the West Nile region of Uganda, Africa, in 1937 and is classified to belong to the Flaviviridae family falvivirus genus (non-patent document 1). The structure of virus particles consists of a spherical structure wherein a capsid protein (C protein) is bonded to one (+) chain RNA virus gene, and a lipid bilayer membrane surrounding the spherical structure. The lipid membrane includes two kinds of proteins: envelope protein (E protein) and membrane protein (M protein). M protein is produced as a precursor prM protein and cleaved with a protease called furin to become a mature protein.

The present inventors previously reported a production method of JEV VLP, comprising introducing an expression vector containing a cDNA fragment encoding prM protein and E protein of Japanese encephalitis virus (JEV) into an animal cell, culturing the obtained transformed cell and harvesting virus-like particles (VLP) secreted in the medium (patent document 1). However, no report has ever been made relating to the production of WNV subunit vaccine.

patent document 1: JP-A-2004-65118
non-patent document 1: Agrawal, A. G., L. R. Petersen, J. Infect. Dis., 188: 1-4 (2003)

DISCLOSURE OF THE INVENTION

Problems to be Solved by the Invention

An object of the present invention is to provide a high secretion production method of WNV VLP useful as a safe and economical WNV vaccine component, thereby enabling the development and stable supply of WNV vaccine. Another object of the present invention is to provide a WNV DNA vaccine capable of producing the aforementioned VLP in the animal body.

Means of Solving the Problems

The present inventors have conducted intensive studies in an attempt to achieve the aforementioned objects and succeeded in efficiently secreting VLP in a medium by introducing an expression vector containing a DNA fragment encoding prM protein and E protein of WNV into an animal cell, and cultivating the obtained transformed cell in the medium. Moreover, the present inventors have found that, unexpectedly, the formation or secretion efficiency of VLP can be remarkably improved as compared to the native full length signal sequence of WNV by altering a signal peptide located upstream of the prM protein.

The present inventor have conducted further studies based on these findings and completed the present invention.

Accordingly, the present invention provides

[1] a signal peptide comprising an amino acid sequence the same or substantially the same as the amino acid sequence of the following (a) or (b)

(a) the amino acid sequence shown by SEQ ID NO: 1
  (b) a partial amino acid sequence of the amino acid sequence of the above-mentioned (a), comprising at least the amino acid sequence shown by amino acid NOs 11-25;

[2] an isolated nucleic acid substantially consisting of a base sequence encoding the signal peptide of the above-mentioned [1];

[3] a West Nile virus-like particle expression vector comprising a nucleic acid comprising a base sequence encoding the signal peptide of the above-mentioned [1], and prM protein and E protein derived from West Nile virus;

[4] a transformant obtained by transformation with the vector of the above-mentioned [3];

[5] a method of producing a West Nile virus-like particle, comprising culturing the transformant of the above-mentioned [4], and recovering a virus-like particle secreted in a medium;

[6] a West Nile virus-like particle obtained by the method of the above-mentioned [5];

[7] a West Nile virus vaccine comprising the particle of the above-mentioned [6] as an active ingredient;

[8] a West Nile virus vaccine comprising the vector of the above-mentioned [3] as an active ingredient, and the like.

Effect of the Invention

By connecting the signal peptide of the present invention to a polyprotein comprised of prM protein and E protein of WNV, the efficiency of formation and extracellular secretion of VLP in a host cell can be improved. Therefore, a secretion expression vector containing the signal peptide, and a nucleic acid encoding prM protein and E protein is useful for the preparation of a WNV VLP highly secreting or producing cell line, and moreover, the vector itself can be used as a WNV DNA vaccine.

BRIEF DESCRIPTION OF THE DRAWINGS

FIG. 1 shows polypeptides encoded by recombinant expression vectors (pWPME1-pWPME14). Polypeptide 1 is MRSSKQKKRGGKT (SEQ ID NO: 23), Polypeptide 2 is MSSKQKKRGGKT (SEQ ID NO: 24), Polypeptide 3 is MSKQKKRGGKT (SEQ ID NO: 25), Polypeptide 4 is MKQKKRGGKT (SEQ ID NO: 26), Polypeptide 5 is MQKKRGGKT (SEQ ID NO: 27), Polypeptide 6 is MKKRGGKT (SEQ ID NO: 28), Polypeptide 7 is MKRGGKT (SEQ ID NO: 29), Polypeptide 8 is MRGGKT (SEQ ID NO: 30), Polypeptide 9 is MGGKT (SEQ ID NO: 31), Polypeptide 10 is MGKT (SEQ ID NO: 32), Polypeptide 11 is MKT, Polypeptide 12 is MT, Polypeptide 13 is MN, and Polypeptide 14 is MS.

FIG. 10 shows the results of comparison by Western blot of the expression level of WNV-like particles after sucrose density gradient centrifugation of the protein secreted in a culture medium by CHO-K1 (parent strain) and each clone acclimated in a serum-free medium, wherein anti-Japanese encephalitis virus (JEV) antibody was used as a primary antibody.

BEST MODE FOR CARRYING OUT THE INVENTION

Figure 2:
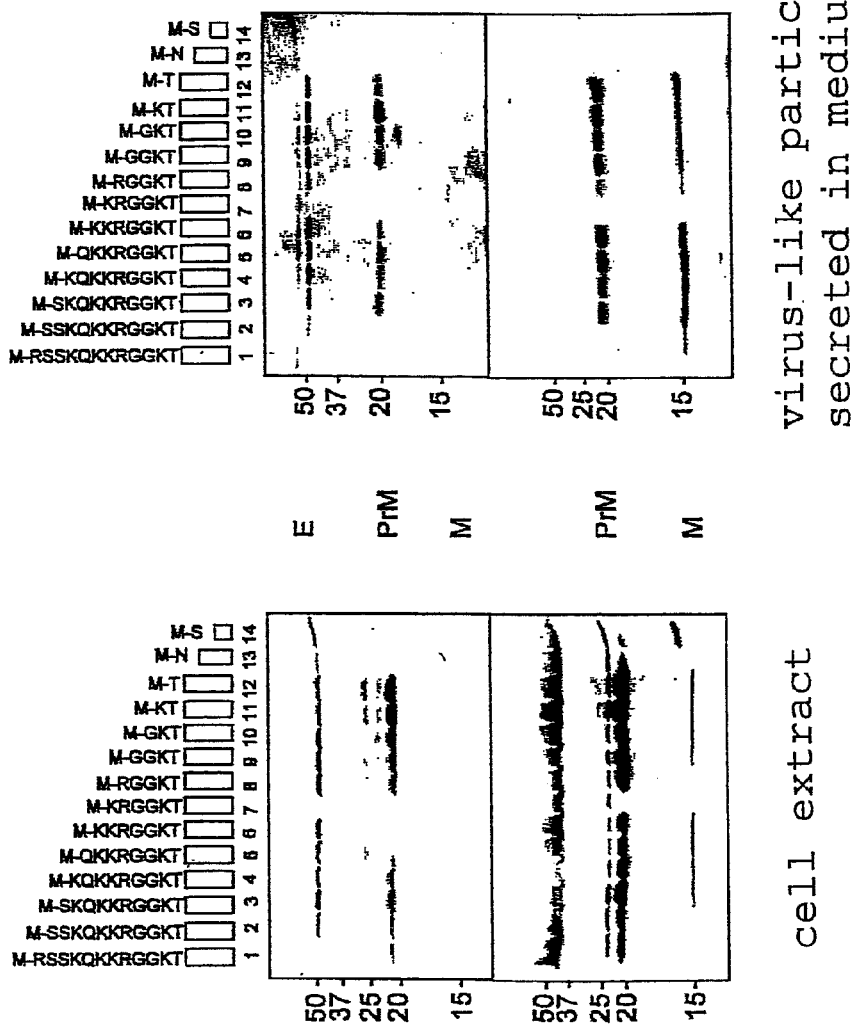
FIG. 2 shows the results of Western blot of WNV E protein expressed and secreted by HEK293 T cells harboring recombinant expression vectors (pWPME1-pWPME14), wherein the left chart shows the results of Western blot of the proteins obtained by solubilizing the cell, and the right chart shows the results of Western blot of the proteins secreted in a culture medium. In the upper left chart and the upper right chart, anti-Japanese encephalitis virus (JEV) antibody was used as a primary antibody, and in the lower left chart and the lower right chart, anti-M protein polyclonal antibody was used as a primary antibody. In the Figures, E, prM and M show the positions of E protein, prM protein and M protein, respectively. Polypeptide 1 is MRSSKQKKRGGKT (SEQ ID NO: 23), Polypeptide 2 is MSSKQKKRGGKT (SEQ ID NO: 24), Polypeptide 3 is MSKQKKRGGKT (SEQ ID NO: 25), Polypeptide 4 is MKQKKRGGKT (SEQ ID NO: 26), Polypeptide 5 is MQKKRGGKT (SEQ ID NO: 27), Polypeptide 6 is MKKRGGKT (SEQ ID NO: 28), Polypeptide 7 is MKRGGKT (SEQ ID NO: 29), Polypeptide 8 is MRGGKT (SEQ ID NO: 30), Polypeptide 9 is MGGKT (SEQ ID NO: 31), Polypeptide 10 is MGKT (SEQ ID NO: 32), Polypeptide 11 is MKT, Polypeptide 12 is MT Polypeptide 13 is MN, and Polypeptide 14 is MS.

The present invention provides a signal peptide for high secretion production of WNV VLP. The signal peptide comprises (a) the amino acid sequence shown by SEQ ID NO: 1;

(b) a partial amino acid sequence of the amino acid sequence of the above-mentioned (a), comprising at least the amino acid sequence shown by amino acid NOs 11-25; or (c) an amino acid sequence the same or substantially the same as the amino acid sequence of the above-mentioned (a) or (b).

Here, the "substantially the same amino acid sequence" is the amino acid sequence of the above-mentioned (a) or (b), wherein one to several (2, 3, 4 or 5) amino acids are substituted, deleted, added or inserted, which has a significantly high WNV VLP secretion ability as compared to WNV native signal sequence.

When "substantially the same amino acid sequence" contains substitution of the amino acid, it is desirably similar to the original amino acid in the physicochemical properties. For example, substitution of amino acids classified into the same group such as aromatic amino acid (Phe, Trp, Tyr), aliphatic amino acid (Ala, Leu, Ile, Val), polar amino acid (Gln, Asn), basic amino acid (Lys, Arg, His), acidic amino acid (Glu, Asp), amino acid having a hydroxyl group (Ser, Thr), amino acid having a small side chain (Gly, Ala, Ser, Thr, Met) and the like can be mentioned. It is predicted that the substitution of such similar amino acids does not change the phenotype of a protein (i.e., preservative amino acid substitution). Specific examples of the preservative amino acid substitution are well known in the art, and described in various documents (see, for example, Bowie et al., Science, 247: 1306-1310 (1990)). When an amino acid (sequence) is substituted, deleted or inserted, the position of the substitution, deletion or insertion is not particularly limited as long as the WNV VLP secretion ability of the original signal peptide is substantially maintained. The "substantially maintained" means having a significantly high secretion ability at least as compared to the native signal sequence of WNV.

The amino acid sequence shown by SEQ ID NO: 1 corresponds to an amino acid sequence of the 99th-123rd (i.e., amino acids from immediately before N terminal of prM protein to 25 amino acid residues in the upstream) of the polyprotein precursor (GenBank Accession No. AAF20092.2) of West Nile virus NY99-flamingo382-99 strain (Lanciotti, R. S. et al., Science, 286: 2333-2337, 1999) (GenBank Accession No. AF196835). Many variants of WNV have been reported so far, and new mutant virus strains will also be found one after another. Thus, an amino acid sequence corresponding to the above-mentioned particular sequence of the NY99-flamingo382-99 strain in such other mutant WNV strains is also encompassed in the "substantially the same amino acid sequence" of the signal peptide of the present invention. Examples of the mutant WNV strain other than the NY99-flamingo382-99 strain include those described in "Table I" of Ebel, G. D. et al., Am. J. Trop. Med. Hyg., 71(4): 493-500, 2004 and the like. The above-mentioned "substantially the same amino acid sequence" can be acquired easily by obtaining a sequence of each Accession No. shown in the Table and determining the corresponding region.

The length of the amino acid sequence of the signal peptide of the present invention is desirably 15 amino acids in the shortest and 25 amino acids in the longest. It preferably has a length other than 20 amino acids. More preferably, the length of the amino acid sequence of the signal peptide is 15-19 or 21-25 amino acids, more preferably 15-18 amino acids.

Therefore, when the "substantially the same amino acid sequence" contains deletion, addition or insertion of amino acids, the number thereof is desirably within a range affording the above-mentioned preferable full-length after alteration. When an amino acid is added or inserted, the kind of the amino acid to be added or inserted is not particularly limited as long as the full-length after the addition or insertion falls within the above-mentioned preferable range.

The signal peptide of the present invention can also be produced by a known peptide synthesis method, for example, a solid phase synthesis process and a liquid phase synthesis process, based on the information of the amino acid sequence thereof. In view of the object of use of the peptide, which is for efficient secretion of WNV VLP from a host cell, the peptide is provided as an N-terminal region of a polyprotein precursor produced by culturing a transformant harboring an expression vector containing a nucleic acid encoding the precursor, wherein the nucleic acid consists of a nucleic acid comprising a base sequence encoding the peptide, which is operably linked to a nucleic acid encoding prM protein and E protein constituting the object VLP.

Therefore, the present invention also provides an isolated nucleic acid substantially consisting of a base sequence encoding the above-mentioned signal peptide of the present invention. Here, "substantially consisting of" means that an amino acid (excluding initiating methionine residue) other than the amino acid sequence of the signal peptide of the present invention is not contained in the N-terminal region (other than prM protein and E protein) of a polyprotein precursor, which is produced by a suitable host cell harboring a suitable expression vector comprising the above nucleic acid operably linked to a nucleic acid encoding the prM protein and E protein of WNV. Therefore, examples of the sequence that can be contained in the nucleic acid besides the base sequence encoding the signal peptide of the present invention include initiating ATG codon, a restriction enzyme recognition sequence that facilitates ligation of the nucleic acid to the downstream of the promoter sequence of an expression vector or the upstream of a nucleic acid encoding prM protein of WNV, and the like.

The nucleic acid may be a DNA or an RNA, or a DNA/RNA chimera, with preference given to DNA. The nucleic acid may be double stranded or single stranded. When the nucleic acid is double stranded, it may be double stranded DNA, double stranded RNA or DNA:RNA hybrid.

The base sequence encoding the above-mentioned signal peptide of the present invention is not particularly limited as long as it generates, after translation, any of the amino acid sequences of the above-mentioned signal peptide of the present invention. When a desired signal peptide is completely the same as a part of a polyprotein precursor sequence of any of the available WNV strains, a base sequence encoding the amino acid sequence can be obtained by PCR method and the like and using, as a template, cDNA prepared from the genomic RNA of the virus strain. Such method is advantageous since not only a signal peptide but also a base sequence encoding prM protein and E protein of WNV can be obtained at once. Depending on the selection of a primer sequence, a nucleic acid encoding signal peptides having different lengths of amino acid sequences can be prepared with ease.

On the other hand, in consideration of the expression efficiency in a host cell, it is generally preferable to select a codon highly frequently used for the host cell to be used. The data of use frequency of codon in various biological species can be obtained from the genetic code use frequency database disclosed, for example, in the home page of Kazusa DNA Research Institute (www.kazusa.or.jp/codon/index.html). For conversion of a base sequence in accordance with codon use frequency of the host cell, the full-length sequence of a nucleic acid encoding a signal peptide is chemically synthesized by a DNA/RNA automatic synthesizer, or partly overlapping oligoDNA short chains synthesized are connected by PCR method.

The present invention also provides a WNV VLP expression vector containing the above-mentioned signal peptide of the present invention, and a nucleic acid comprising a base sequence encoding prM protein and E protein derived from WNV.

Here, the "base sequence encoding prM protein of WNV" means a base sequence encoding a protein comprising an amino acid sequence the same or substantially the same as the amino acid sequence shown by SEQ ID NO: 3. The "base sequence encoding E protein of WNV" means a base sequence encoding a protein comprising an amino acid sequence the same or substantially the same as the amino acid sequence shown by SEQ ID NO: 5.

As the "amino acid sequence substantially the same as the amino acid sequence shown by SEQ ID NO: 3 (or SEQ ID NO: 5)", an amino acid sequence having a homology of not less than about 80%, preferably not less than about 90%, more preferably not less than about 95%, particularly preferably not less than about 97%, with the amino acid sequence shown by SEQ ID NO: 3 (or SEQ ID NO: 5) and the like can be mentioned.

Here, "homology" means a ratio (%) of amino acid residues identical or similar to all overlapping amino acid residues in the optimal alignment where two amino acid sequences are aligned using a mathematical algorithm known in the technical field (preferably, the algorithm can consider introduction of gaps on one or both of the sequences for the best alignment). The "similar amino acid" refers to an amino acid similar in its physiochemical properties, and examples include amino acids classified in the same group as the original amino acids in, for example, a classification similar to the aforementioned classification of the signal peptide of the present invention.

Homology of the amino acid sequences in the present specification can be measured under the following conditions (an expectation value=10; gaps are allowed; matrix=BLOSUM62; filtering=OFF) using a homology scoring algorithm NCBI BLAST (National Center for Biotechnology Information Basic Local Alignment Search Tool). Other algorithm for determining homology of the amino acid sequence is exemplified by an algorithm disclosed in Karlin et al., Proc. Natl. Acad. Sci. USA, 90: 5873-5877 (1993) [this algorithm is incorporated in NBLAST and XBLAST program (version 2.0) (Altschul et al., Nucleic Acids Res., 25:3389-3402 (1997))]; an algorithm disclosed in Needleman et al., J. Mol. Biol., 48: 444-453 (1970) [This algorithm is incorporated in a GAP program in a GCG software package]; an algorithm disclosed in Myers and Miller, CABIOS, 4: 11-17 (1988) [This algorithm is incorporated in ALIGN program (version 2.0) which is a part of a CGC sequence alignment software package]; an algorithm disclosed in Pearson et al., Proc. Natl. Acad. Sci. USA, 85: 2444-2448 (1998) [This algorithm is incorporated in an FASTA program in a GCG software package], etc., and these may be also preferably used.

More preferably, the "amino acid sequence substantially the same as the amino acid sequence shown by SEQ ID NO: 3 (or SEQ ID NO: 5)" is an amino acid sequence having an identity of not less than about 80%, preferably not less than about 90%, more preferably not less than about 95%, particularly preferably not less than about 97%, with the amino acid sequence shown by SEQ ID NO: 3 (or SEQ ID NO: 5).

The "protein comprising an amino acid sequence substantially the same as the amino acid sequence shown by SEQ ID NO: 3 (or SEQ ID NO: 5)" means a protein comprising an amino acid sequence substantially the same as the aforementioned amino acid sequence shown by SEQ ID NO: 3 (or SEQ ID NO: 5), and having substantially identical activity as a protein comprising the amino acid sequence shown by SEQ ID NO: 3 (or SEQ ID NO: 5).

"Substantially identical activity" in the case of prM protein is, for example, an activity to change conformation of E protein when it has matured as M protein, and the like, and that of E protein is, for example, adsorption to infected host cell, red blood cell coagulation activity and the like. "Substantially identical" means that these activities are qualitatively the same. Therefore, each of the above-mentioned activities are preferably equivalent (e.g., about 0.5- to about 2-fold), but quantitative factors such as the extent of activity and protein molecular weight may be different.

The prM protein (E protein) to be used in the present invention includes, for example, a protein comprising (1) an amino acid sequence shown by SEQ ID NO: 3 (or SEQ ID NO: 5) m wherein one or more (preferably about 1-30, more preferably about 1-10, still more preferably 1-several (2, 3, 4 or 5)) amino acids are deleted, (2) an amino acid sequence shown by SEQ ID NO: 3 (or SEQ ID NO: 5) wherein one or more (preferably about 1-30, more preferably about 1-10, still more preferably 1-several (2, 3, 4 or 5)) amino acids are added, (3) an amino acid sequence shown by SEQ ID NO: 3 (or SEQ ID NO: 5) wherein one or more (preferably about 1-30, more preferably about 1-10, still more preferably 1-several (2, 3, 4 or 5)) amino acids are inserted, (4) an amino acid sequence shown by SEQ ID NO: 3 (or SEQ ID NO: 5) wherein one or more (preferably about 1-30, more preferably about 1-10, still more preferably 1-several (2, 3, 4 or 5)) amino acids are substituted by other amino acids, (5) a combination of such amino acid sequences, or the like.

When an amino acid sequence is inserted, deleted or substituted as mentioned above, the position of the insertion, deletion or substitution is not particularly limited as long as the activity of protein is maintained.

DNA encoding prM protein (or E protein) of WNV can be directly amplified by Reverse Transcriptase-Polymerase Chain Reaction (hereinafter to be abbreviated as "RT-PCR method") and using RNA prepared from a virus stock of WNV as a template. Since prM protein and E protein are continuously encoded in the WNV genome, DNAs encoding prM protein and E protein can be prepared at once by designing a primer capable of amplifying a base sequence covering the coding regions of the both. Moreover, when a sequence in the WNV genome is utilized as a base sequence encoding the signal peptide of the present invention, since the signal peptide coding region is present immediately before the coding region of prM protein, the three can also be prepared at once.

Examples of the DNA encoding prM protein (or E protein) include a DNA containing a base sequence shown by SEQ ID NO: 2 (or SEQ ID NO: 4), a DNA containing a base sequence that hybridizes with a complementary chain sequence of the base sequence shown by SEQ ID NO: 2 (or SEQ ID NO: 4) under stringent conditions, and encoding a protein having a substantially identical activity to the aforementioned prM protein (or E protein), and the like.

Examples of the DNA capable of hybridizing to the base sequence shown by SEQ ID NO: 2 (or SEQ ID NO: 4) under stringent conditions include DNA containing a base sequence having not less than about 70%, preferably not less than about 80%, more preferably not less than about 90%, and particularly preferably not less than about 95%, homology to the base sequence shown by SEQ ID NO: 2 (or SEQ ID NO: 4) and the like.

The homology of the base sequence in the present specification can be calculated using homology calculation algorithm NCBI BLAST (National Center for Biotechnology Information Basic Local Alignment Search Tool) under the following conditions (expectancy=10; gaps are allowable; filtering=ON; match score=1; mismatch score=−3). Examples of other algorithms to determine a homology of base sequence preferably include the above-mentioned homology calculation algorithms of amino acid sequence in a similar manner.

Hybridization can be conducted according to a method known per se or a method based thereon, for example, a method described in Molecular Cloning, 2nd edition (J. Sambrook et al., Cold Spring Harbor Lab. Press, 1989) and the like. When a commercially available library is used, hybridization can be conducted according to the method described in the instruction manual attached thereto. Hybridization can preferably be conducted under highly stringent conditions.

Examples of the stringent conditions include a hybridization reaction in 6×SSC (sodium chloride/sodium citrate) at 45° C., and then one or more times of washing in 0.2×SSC/ 0.1% SDS at 65° C., and the like. Those of ordinary skill in the art can easily adjust to a desired stringency by appropriately changing the salt concentration of hybridization solution, the temperature of hybridization reaction, probe concentration, probe length, number of mismatch, hybridization reaction time, salt concentration of washing, washing temperature and the like.

A DNA encoding prM protein and E protein can be obtained from WNV genome as mentioned above. It is also possible to construct a DNA encoding the full length of prM protein and E protein by chemically synthesizing a DNA chain, or connecting, by PCR method, partly overlapping oligoDNA short chains synthesized. The advantage of constructing a full-length DNA by combining chemical synthesis or PCR method is that, as mentioned above, the codon to be used can be designed over the full length of the gene according to the host into which the gene is to be introduced.

The DNA cloned as mentioned above can be used as is, or after digestion with a restriction endonuclease or addition of a linker as desired, depending on the purpose of its use. When DNA encoding signal peptide, DNA encoding prM protein and DNA encoding E protein are individually cloned, they are ligated in the above-mentioned order by using suitable restriction enzyme, linker, ligase and the like.

Then, the obtained DNA encoding "signal peptide-prM protein-E protein" polyprotein precursor, after introduction as necessary of ATG as a translation initiation codon into the 5' terminal side, and TAA, TGA or TAG as a translation stop codon into the 3' terminal side, is ligated to the downstream of a promoter in a suitable expression vector by using a restriction enzyme and a DNA ligase. The translation initiation codons and translation stop codons can be added to using an appropriate synthetic DNA adapter. Alternatively, utilizing PCR in advance, they may be introduced into the 5' side of a base sequence encoding the signal peptide and the 3' side of a base sequence encoding E protein, respectively.

Useful expression vectors include plasmids derived from *Escherichia coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); insect cell expression plasmids (e.g., pFast-Bac); animal cell expression plasmids (e.g., pCAGGS, pA1-11, pXT1, pRc/CMV, pRc/RSV, pcDNAI/Neo); bacteriophages such as λ phage; insect viral vectors such as baculovirus (e.g., BmNPV, AcNPV); animal viral vectors such as retrovirus, vaccinia virus, adenovirus; and the like.

The promoter may be any promoter, as long as it is appropriate for the host used to express the gene.

For example, when the host is an animal cell, useful promoters include CAG promoter, β-actin promoter, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (simple herpes virus thymidine kinase) promoter and the like are used. Among these, CAG promoter is preferable.

When the host is a bacterium of the genus *Bacillus*, the SPO1 promoter, the SPO2 promoter, the penP promoter and the like are preferred.

When the host is yeast, the PHO5 promoter, the PGK promoter, the GAP promoter, the ADH promoter and the like are preferred.

When the host is an insect cell, the polyhedrin promoter, the P10 promoter and the like are preferred.

Useful expression vectors include, in addition to the above, those optionally harboring an enhancer, a splicing signal, a polyA addition signal, a selection marker, an SV40 replication origin (hereinafter sometimes to be abbreviated as SV40 ori) and the like. As examples of the selection marker, dihydrofolate reductase gene (hereinafter sometimes to be abbreviated as dhfr, methotrexate (MTX) resistant), ampicillin is resistant gene (hereinafter sometimes to be abbreviated as $amp^r$), neomycin resistance gene (hereinafter sometimes to be abbreviated as $neo^r$, G418 resistant) and the like can be mentioned. In particular, when a dhfr-deficient Chinese hamster ($CHO-dhfr^-$) cell is used in combination with the dhfr gene as the selection marker, a target gene can also be selected using a thymidine-free medium.

WNV VLP can be produced by culturing a transformant obtained by transforming a host with an expression vector containing a nucleic acid comprising a base sequence encoding the signal peptide of the present invention, prM protein and E protein.

Useful hosts include, for example, those suitable for secretion expression such as bacterium of the genus *Bacillus*, yeast, an insect cell, an insect, an animal cell, an animal and the like.

Useful bacteria of the genus *Bacillus* include, for example, *Bacillus subtilis* MI114, 207-21 and the like.

Useful yeasts include, for example, *Saccharomyces cerevisiae* AH22, $AH22R^-$, NA87-11A, DKD-5D and 20B-12, *Schizosaccharomyces pombe* NCYC1913 and NCYC2036, *Pichia pastoris* KM71, and the like.

Useful insect cells include, for example, *Spodoptera frugiperda* cell (Sf cell), MG1 cell derived from the mid-intestine of *Trichoplusia ni*, High Five™ cell derived from an egg of *Trichoplusia ni*, cell derived from *Mamestra brassicae*, cell derived from *Estigmena acrea*, and the like can be mentioned when the virus is AcNPV. When the virus is BmNPV, useful insect cells include *Bombyx mori* N cell (BmN cell) and the like. Useful Sf cells include, for example, Sf9 cell (ATCC CRL1711), Sf21 cell and the like.

Useful insects include, for example, a larva of *Bombyx mori* and the like.

Useful animal cell includes, for example, cells such as COS-7, Vero, CHO, CHO ($dhfr^-$, CHO-K1, L, AtT-20, GH3, FL, HEK293, NIH3T3, Balb3T3, FM3A, L929, SP2/0, P3U1, B16, P388 and the like. Preferably, HEK293, CHO-K1 and the like are used but the animal cell is not limited thereto.

As the animal, mammals with established transgenic system (e.g., mouse, rat, rabbit, sheep, swine, bovine), chicken and the like can be mentioned.

Transformation can be carried out according to the kind of host in accordance with a publicly known method.

A bacterium of the genus *Bacillus* can be transformed, for example, in accordance with the method described in Molecular & General Genetics, vol. 168, 111 (1979) and the like.

Yeast can be transformed, for example, in accordance with the method described in Methods in Enzymology, Vol. 194, 182-187 (1991), Proc. Natl. Acad. Sci. USA, Vol. 75, 1929 (1978) and the like.

An insect cell and an insect can be transformed, for example, according to a method described in Bio/Technology, 6, 47-55 (1988) and the like.

An animal cell can be transformed, for example, in accordance with the method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

An animal can be transformed, for example, in accordance with the method described in Development of Transgenic Animal (CMC Publishing) (2001).

A transformant can be cultured in accordance with a known method according to the kind of the host.

For culture of a transformant with the genus *Bacillus* as a host, for example, the medium to be used for the culture is preferably a liquid medium. In addition, the medium preferably contains a carbon source, a nitrogen source, an inorganic substance and the like, which are necessary for the growth of a transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. In addition, the medium may contain a yeast extract, vitamins, a growth promoting factor and the like. The medium has a pH of preferably about 5-about 8. A transformant is cultured generally at about 30-about 40° C. for about 6-about 24 hr. Where necessary, aeration and stirring may also be performed.

Examples of the medium for culture of a transformant with yeast as a host include Burkholder minimum medium, SD medium containing 0.5% casamino acid and the like. The medium has a pH of preferably about 5-about 8. Culture is performed generally at about 20-about 35° C. for about 24-about 72 hr. Where necessary, aeration and stirring may also be performed.

Examples of the medium for culture of a transformant with an insect cell or insect as a host include Grace's Insect Medium appropriately supplemented with an additive such as inactivated 10% bovine serum and the like, and the like. The medium has a pH of preferably about 6.2-about 6.4. Culture is performed generally at about 27° C. for about 3-about 5 days. Where necessary, aeration and stirring may also be performed.

Examples of the medium for culture of a transformant with an animal cell as a host include minimum essential medium (MEM), Dulbecco's modified Eagle medium (DMEM), RPMI 1640 medium, 199 medium and the like, containing about 5-about 20% of fetal bovine serum. The medium has a pH of preferably about 6-about 8. Culture is performed generally at about 30° C.-about 40° C. for about 15-about 60 hr. Where necessary, aeration and stirring may also be performed.

When the host is an animal, a transgenic animal is obtained from a transgenic fertilized egg according to a conventional method and bred under general breeding conditions, and mammalian milk or chicken egg is obtained.

In the above manner, WNV VLP can be secreted in the medium of a transformant or extracellularly.

In the present invention, moreover, a transformant may be cultured in a medium containing fetal bovine serum as mentioned above. However, from the aspects of removal of a risk factor such as bovine viral diarrhea virus (BVDV) that enters fetal bovine serum to contaminate cells and the like, removal of impurity such as bovine-derived protein and the like in an attempt to simplify a WNV VLP purification step, and economical aspect, a method including culturing a transformant with serum-free acclimation is also preferably used. As described in the below-mentioned Examples, it is preferable to obtain a non-adherent cell from an adherent cell by acclimation in a serum-free medium, since it facilitates maintenance, passage and mass culture of the transformant.

VLP secreted in a medium (extracellularly) can be purified by a method known per se. For example, VLP can be prepared by filtering a recovered medium (extracellular liquid) to remove low molecular weight proteins, and applying the medium to sucrose density gradient centrifugation.

The WNV vaccine of the present invention contains WNV VLP as an active ingredient in an amount sufficient to provide immunity. Specifically, for example, WNV vaccine can be produced as in the following, though not limited thereto.

VLP of the present invention purified as an antigen are suspended in a solvent such as an isotoic salt solution, buffer, tissue culture liquid and the like, for example, PBS (phosphate buffered saline) to give a vaccine stock solution. Where necessary, a vaccine antigen may be immobilized with a conventional immobilizer to also immobilize the steric structure thereof. Examples of the immobilizer include formalin, phenol, glutardialdehyde, β-propiolactone and the like. The immobilizer may be add to an antigen before preparation of a vaccine stock solution, or added to a vaccine stock solution.

Then, a vaccine stock solution is diluted to give a vaccine solution. A vaccine stock solution is diluted, for example, with PBS so that the amount of the antigen in the vaccine will be sufficient to induce antibody production to afford immunity, for example, 1-20 µg/ml, preferably 10 µg/ml, in a protein content. For preparation of a vaccine solution, a stabilizer that potentiates heat resistance of vaccine and an adjuvant as an auxiliary to enhance immunogenicity may be added. As the stabilizer, saccharides and amino acids can be mentioned. As the adjuvant, mineral oil, vegetable oil, alum, aluminum compound, bentonite, silica, muramyl dipeptide derivative, thymosin, interleukin and the like can be mentioned.

A vaccine solution is dispensed in a container with a suitable volume, for example, about 0.5-20 ml vial, and the container is tightly sealed and used as a vaccine. Such vaccine may be a liquid or freeze-dried after dispensing and used as a dry preparation.

The vaccine of the present invention may be inoculated to a subject in the same manner as with general vaccines. For example, about 0.2-0.5 ml of a vaccine for one dose can be subcutaneously inoculated 1-3 times at about 1-4 weeks intervals. A dry preparation is dissolved in sterile distilled water and the like before inoculation to the original volume and thereafter used.

Since an expression vector (non-virus vector and virus vector) containing the above-mentioned signal peptide of the present invention, and a nucleic acid comprising a base sequence encoding prM protein and E protein of WNV can efficiently secrete WNV VLP in the human body after administration thereof to human, it can be used as what is called a DNA vaccine.

Preferable production methods, administration methods and the like of these non-virus vector and virus vector are known to those of ordinary skill in the art and, for example, Experimental Medicine, extra issue, basic technique of gene therapy, YODOSHA, 1996; Experimental Medicine, extra issue, Transgene & Expression Analysis Experiment Method, YODOSHA, 1997; ed. Japan Society of Gene Therapy, Gene Therapy Development Research Handbook, NTS, 1999 and the like are used for reference. Examples of the non-virus vector suitable for DNA vaccines include, but are not limited to, pcDNA3.1, pZeoSV, pBK-CMV (Invitrogen, Stratagene), pCAGGS (Gene 108, 193-200 (1991)) and the like. Representative virus vector includes virus vectors such as recombinant adenovirus, retrovirus and the like. Specifically, for example, DNA viruses such as detoxicated retrovirus, adenovirus, adeno-associated virus, herpes virus, vaccinia virus, pox virus, polio virus, sindbis virus, Hemagglutinating Virus of Japan, SV40, human immunodeficiency virus (HIV) and the like and RNA virus can be mentioned.

As a method for introducing the DNA vaccine of the present invention into human, an in vivo method including directly introducing a DNA vaccine into the body, an ex vivo method including taking out a certain cell from human, extracellularly introducing a DNA vaccine into the cell and returning the cell into the body and the like can be mentioned (ed. Japan Society of Gene Therapy, Gene Therapy Development Research Handbook, NTS, 1999). According to the in vivo method, the DNA vaccine of the present invention is dissolved in a suitable solvent (buffer such as PBS and the like, saline, sterile water etc.), sterilized by filtration with a filter etc. as necessary, filled in an aseptic container to give an injection, which is administered to human by injection. Injection may contain a conventional carrier and the like as necessary. In addition, a DNA vaccine may also be enclosed in a liposome made of a lipid bilayer membrane, and administered as an HVJ-liposome obtained by fusion of the liposome and inactivated Hemagglutinating Virus of Japan (HVJ) (Experimental Medicine, extra issue, basic technique of gene therapy, YODOSHA, 1996; Transgene & Expression Analysis Experiment Method, YODOSHA, 1994). The DNA vaccine of the present invention can be administered to the muscle, skin, nasal cavity and the like. As the ex vivo method, a lipofection method, a phosphoric acid-calcium coprecipitation method, a DEAE-dextran method, a method including direct injection of DNA vaccine intracellularly using a tiny glass tube and the like, and the like can be mentioned.

While the dose of the DNA vaccine of the present invention varies depending on the administration target, administration method, administration manner and the like, it is generally about 500 μg-about 50 mg, preferably about 500 μg-about 1 mg, per adult based on the gene.

The present invention is explained in more detail in the following by referring to Examples, which are not to be construed as limitative.

EXAMPLES

Example 1

Production of Recombinant Expression Vector Expressing WNV-Derived Mutated Signal Peptide Sequence, prM Protein and E Protein Polyadenylated RNA was extracted from WNV (WN-NY99), and using same as a template and 15 nucleotide poly(dT) primer, a reverse transcription reaction was performed with SuperScript RNase H⁻ reverse transcriptase (Invitrogen Life Technologies, Carlsbad, Calif.). The coding region of the obtained WNV cDNA was amplified by PCR by using a complementary primer set (base sequences shown by SEQ ID NO: 6 and SEQ ID NO: 7). The obtained PCR product was digested with BglII and XhoI, and subcloned to pBluescript plasmid. Using the obtained plasmid as a template and a primer set complementary to the base sequence encoding a signal sequence defective in one amino acid from the amino terminal side (one base sequence selected from the group consisting of SEQ ID NOs: 8-21 and one base sequence shown by SEQ ID NO: 22), DNA fragment was amplified by PCR. The amplified fragment was subcloned to a mammal expression vector (pCAGGS) to give 14 kinds of recombinant expression vectors expressing signal sequence having a particular length, prM protein and E protein (pWPME1-pWPME14). The structure of polypeptide encoded by the obtained PCR product is shown in FIG. 1.

Example 2

Consideration of Signal Peptide Sequence Having Length within Range Suitable for Secretion Various recombinant expression vectors (0.5 μg) obtained in Example 1 were introduced into HEK293T cells (2×10⁵) using Fugene 6 (Roche Diagnostic, Basel, Switzerland). After 48 hr, the cells were washed twice with phosphate buffered saline (PBS), and solubilized with a solubilizing solution containing 50 mM Tris-HCl (pH 6.8), 100 mM ditiothreitol, 2% sodium dodecyl sulfate (SDS), 0.1% bromophenol blue and 10% glycerol. On the other hand, the culture supernatant was filtered (0.45 μm pore size, Millipore, Bedford, Mass.), and subjected to an ultracentrifugation treatment at 40,000×g for 30 min. The residue was solubilized with the aforementioned solubilizing solution.

According to a conventional method, the WNV-like particles obtained in the above were subjected to SDS-PAGE, membrane transcription and Western blot using an antibody. Specifically, protein was separated by 10% PAGE, and the separated protein was transcribed to a polyvinyl difluoride (PDVF) membrane filter (Millipore). As primary antibodies, an anti-Japanese encephalitis virus (JEV) antibody that cross reacts with WNV and an anti-M protein polyclonal antibody (IMGENEX, San Diego, Calif.) were used, and as a secondary antibody, anti-rabbit IgG (Pierce, Rockford, Ill.) conjugated with horseradish peroxidase was used. For luminescence, ECL reagent (Amersham Pharmacia Biotech, Piscataway, N.J.) was used, and the luminescence was detected by a LAS1000 imaging system (Fujifilm, Tokyo, Japan). The expression of the WNV-like particles between various recombinant expression vectors is shown in FIG. 2.

Moreover, according to the method described in Kojima, A., A. Yasuda, H. Asanuma, T. Ishikawa, K. Yasui, T. Kurata. J. Viorl 77: 8745-55 (2003), E protein antigens secreted in the culture media was compared between the above-mentioned respective recombinant expression vectors by sandwich ELISA method using a monoclonal antibody (402) to E protein antigen.

Figure 3:
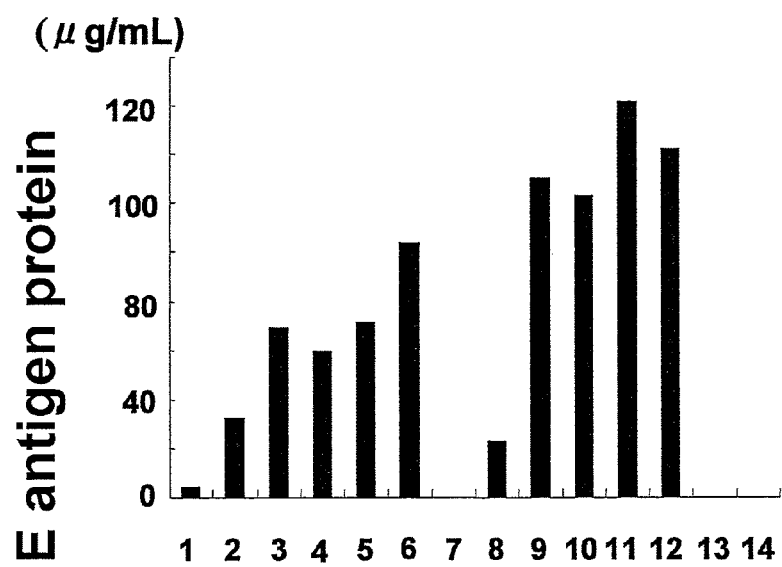
FIG. 3 shows the results of comparison by the sandwich ELISA method of quantified E proteins secreted in a culture medium by HEK293T cells harboring recombinant expression vectors (pWPME1-pWPME14), wherein 402 monoclonal antibody was used as a primary antibody.

Specifically, E protein antigens were bound using a microplate (Corning Incorporated Life Sciences, Acton, Mass.) coated with 402 antibody. The bound E protein antigens were detected using 402 antibody (TMB; DAKO Corp., Carpinteria, Calif.) m conjugated with horseradish peroxidase as a substrate. Comparison of secretion amounts of the WNV-like particles between various recombinant expression vectors is shown in FIG. 3.

Figure 4:
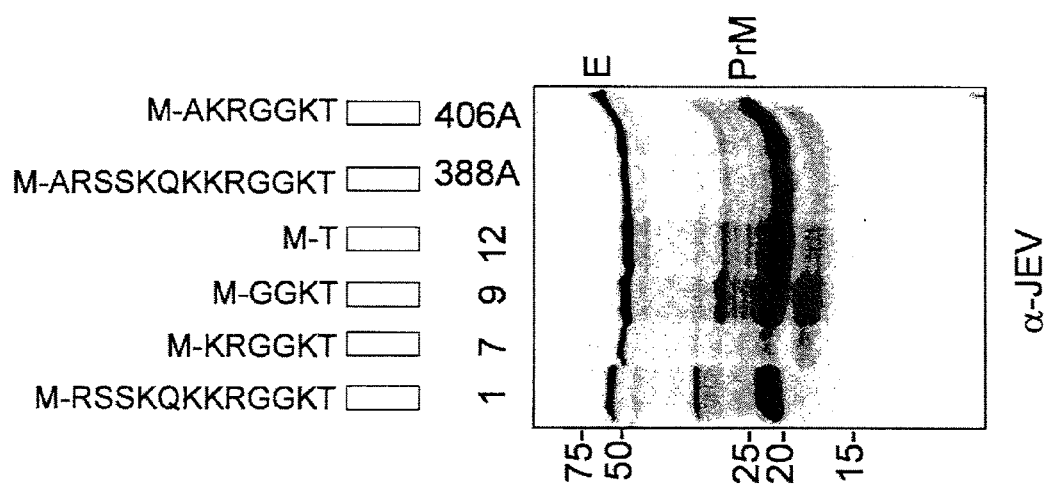
FIG. 4 shows the results of Western blot of WNV E proteins expressed by HEK293T cells harboring recombinant expression vectors (pWPME1, 7, 9, 12, pWPME388A, pWPME406A). An anti-Japanese encephalitis virus (JEV) antibody was used as a primary antibody, wherein E and prM show the positions of E protein and prM protein, respectively. The WNV-E proteins include MAKRGGKT (SEQ ID NO: 33), MARSSKQKKRGGKT (SEQ ID NO: 34), MT, MGGKT (SEQ ID NO: 35), MKRGGKT (SEQ ID NO: 36), and MRSSKQKKRGGKT (SEQ ID NO: 37).
Figure 5:
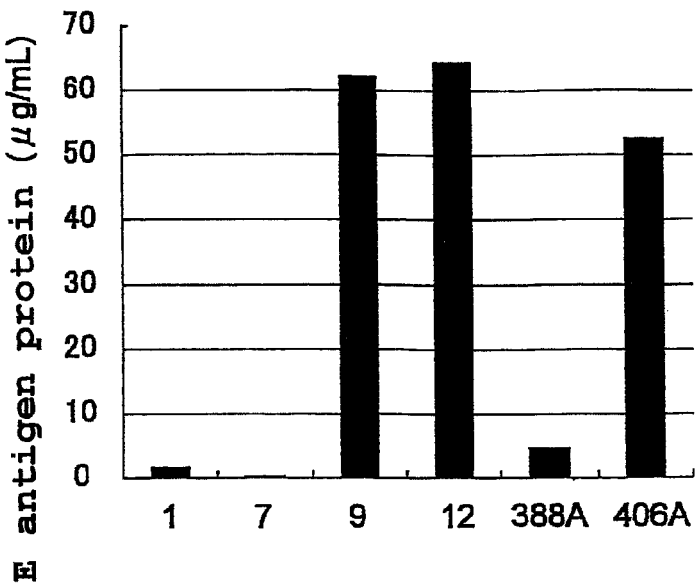
FIG. 5 shows the results of comparison by the sandwich ELISA method of quantified E proteins secreted in a culture medium by HEK293T cells harboring recombinant expression vectors (pWPME1, 7, 9, 12, pWPME388A, pWPME406A), wherein 402 monoclonal antibody was used as a primary antibody.

In addition, recombinant expression vectors (pWPME388A, pWPME406A) obtained by adding alanine to immediately after starting amino acid of recombinant expression vectors pWPME1 and pWPME7 were produced, and the expression level was compared between various recombinant expression vectors by the above-mentioned method. The results are shown in FIGS. 4 and 5. From these results, it was found that the length of signal sequence greatly affects the expression and secretion of WNV-like particles.

Example 3

Observation Image of WNV-Like Particles by Electron Microscope

Figure 6:
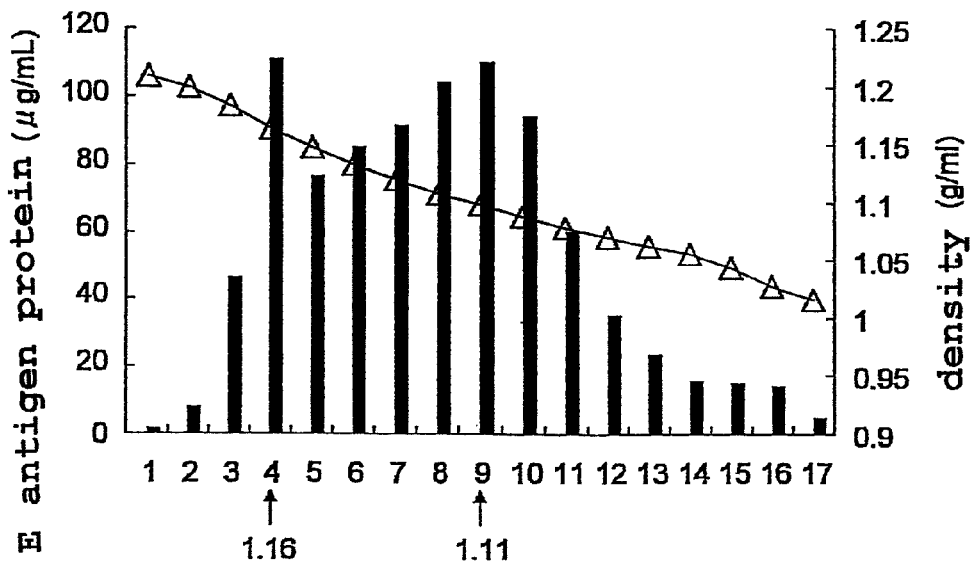
FIG. 6 shows the results of comparison by the sandwich ELISA method of quantified E proteins in each sample fraction after sucrose density gradient centrifugation of the protein secreted in a culture medium by HEK293T cell harboring a recombinant expression vector (pWPME12).

The recombinant expression vector pWPME12 obtained in Example 1 was introduced into HEK293T cells, and the medium was collected 48 hr later. The collected medium was filtered (0.45 μm, Millipore) and purified (Biomax-100 membrane filter, Millipore). WNV-like particles obtained by removing protein small molecules having a molecular weight of less than 100 kDa were applied to 10-45% (w/w) sucrose density gradient centrifugation (150,000×g, 14 hr). The density and E protein antigen amount of sample fractions 1-17 were measured according to the above-mentioned ELISA method. As the result, a peak of E protein antigen was observed in sample fraction 9 having a density of 1.11 and sample fraction 4 having a density of 1.16 (FIG. 6).

Figure 7:
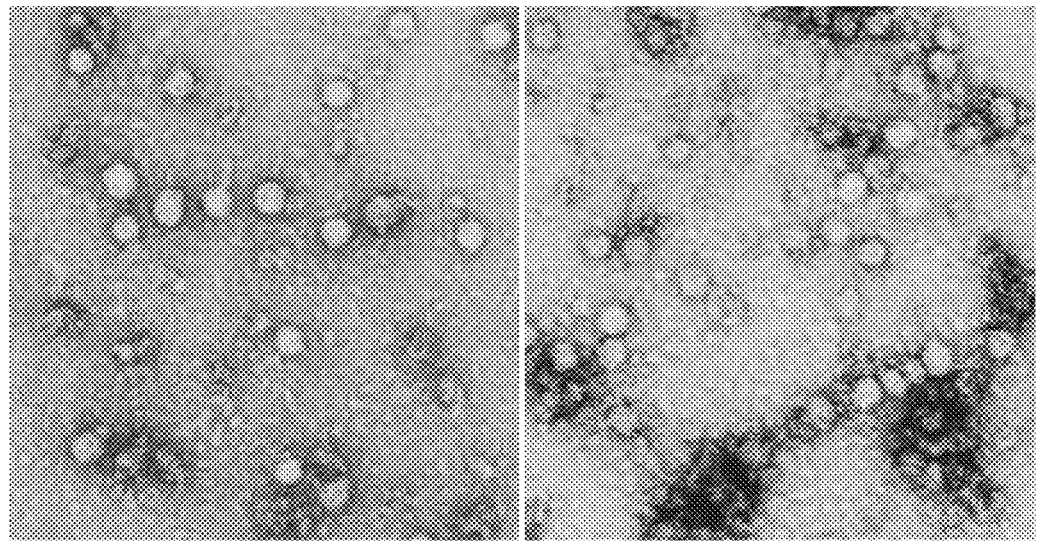
FIG. 7 shows electron microscopic images of WNV-like particles secreted in a culture medium by HEK293T cells harboring a recombinant expression vector (pWPME12). The left charts show virus-like particles contained in sample fractions with density 1.16, and the right charts show virus-like particles contained in sample fractions with density 1.11.
Figure 7:
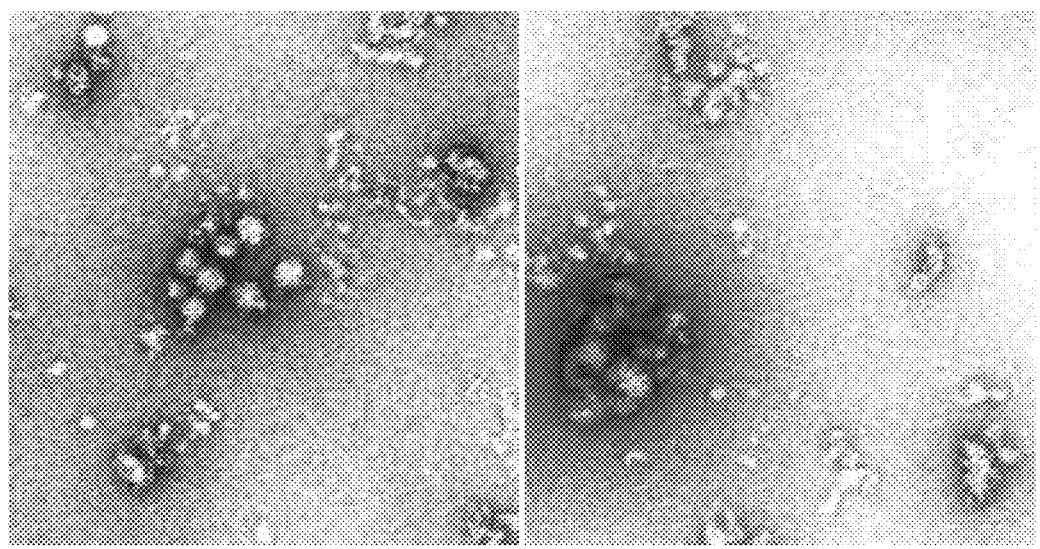
Figure 8:
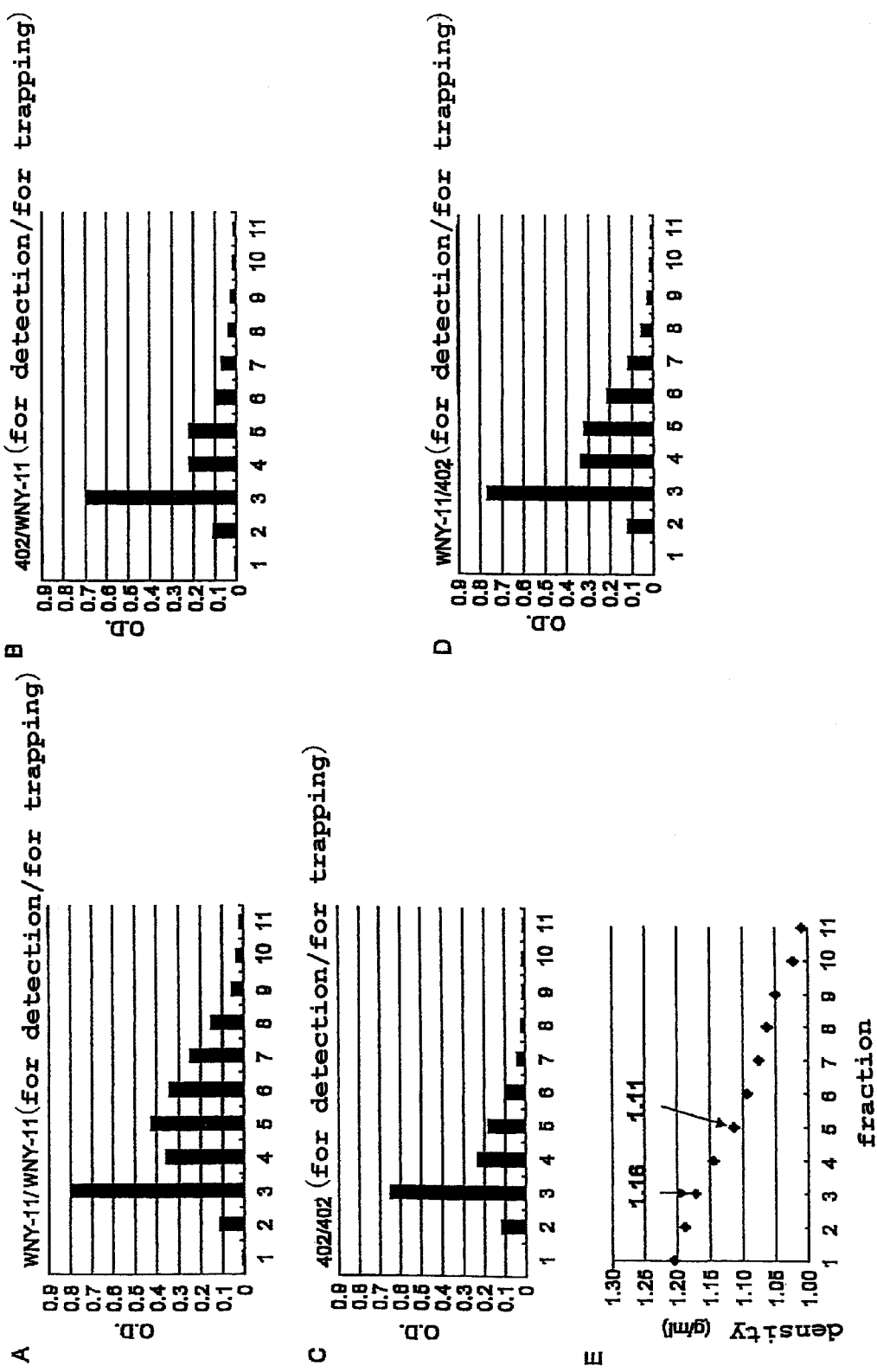
FIG. 8 shows the results of quantification by the sandwich ELISA method of E proteins in each sample fraction after sucrose density gradient centrifugation of the protein secreted in a culture medium by HEK293T cells harboring a recombinant expression vector (pWPME12). A shows the results obtained by using WNY-11 as a trapping antibody and WNY-11 as a detection antibody. B shows the results obtained by using WNY-11 antibody as a trapping antibody and 402 antibody as a detection antibody. C shows the results obtained by using 402 antibody as a trapping antibody and 402 antibody as a detection antibody. D shows the results obtained by using 402 antibody as a trapping antibody and WNY-11 antibody as a detection antibody. E shows the density of each sample fraction.
Figure 9:
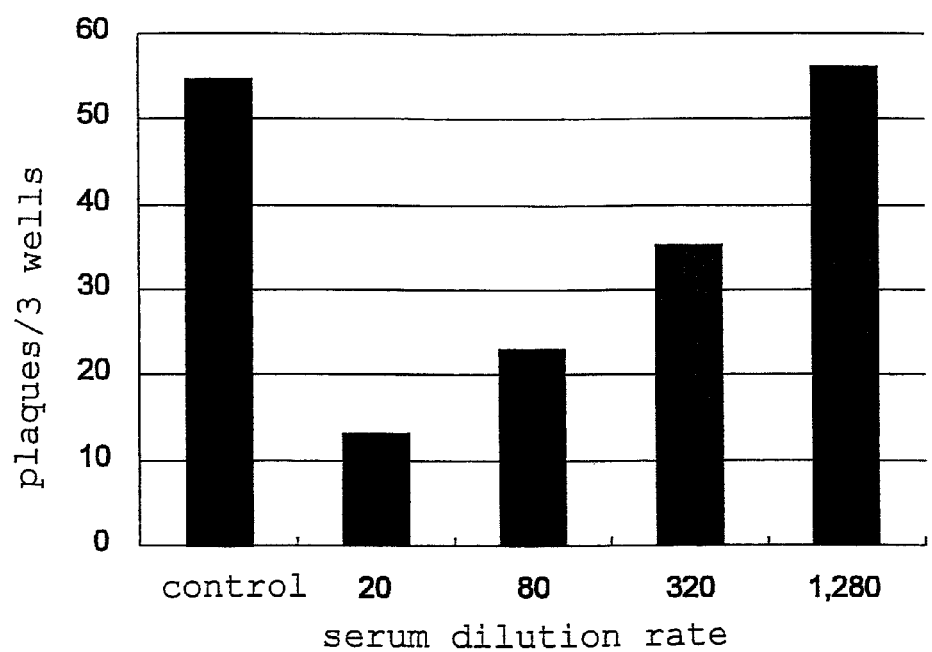
FIG. 9 shows the results of a plaque decrease assay of WNV by using the serum of mouse immunized with WNV-like particles, wherein the serum used was diluted and the plaque number is the total of 3 wells.

A low molecular weight mixture was removed from E protein antigen contained in the two sample fractions 4 and 9 obtained in the above by Sephadex G-25 column (Hiprep; Amersham Pharmacia Bioteck) chromatography, and E protein antigen was eluted with phosphate buffered saline and preserved at 4° C. The obtained purified antigen was subjected to negative staining with sodium phosphotungstate using a grid coated with copper formvar. The specimen was observed with a JOEL 1200 Ex electron microscope (Hitachi, Tokyo, Japan). As a result, sample fraction 9 was confirmed to have many particles with diameter of about 30 nm and having a spherical structure (FIG. 7, right side). On the other hand, in sample fraction 4, particles (diameter about 25 nm) having various forms and coated with a staining fluid were occasionally seen (FIG. 7, left side).

Example 4

Epitope Analysis for Inducing WNV-Like Particle Neutralization Antibody

The recombinant expression vector pWPME12 obtained in Example 1 was introduced into HEK293T cells, and the obtained E protein antigen was subjected to sucrose density gradient centrifugation to give sample fractions 1-11 (FIG. 8E). According to the above-mentioned ELISA method, sample fractions with high content of E protein antigen having neutralization epitope were found by using WNY-11 antibody (WNV neutralization antibody) and 402 antibody (non-neutralization antibody) as antibody for capture or antibody for detection. As a result, when the WNY-11 antibody was used as an antibody for capture and an antibody for detection, a peak could be confirmed in sample fraction 3 (density 1.16) and sample fraction 5 (density 1.11) (FIG. 8A). On the other hand, when the WNY-11 antibody and 402 antibody were used as antibody for capture and/or antibody for detection, the content of E protein antigen in sample fraction 5 decreased as compared to the use only of WNY-11 antibody (FIG. 8B-D). The neutralization epitope recognized by WNY-11 in sample fraction 3 seems to be less than that in sample fraction 5.

Example 5

Consideration of Induction Property of Neutralization Antibody

Using plural fractions including sample fractions 3 and 5 prepared in Example 4, whether or not induction of neutralization antibody in mouse was possible was considered. To be specific, BALB/c mouse was intraperitoneally immunized twice with adjuvant-conjugated WNV-like particles (about 300 ng, 1/16 of weight of formulation of Japanese encephalitis vaccine to human) at 7 day intervals. At 3 weeks from the second immunization, neutralization antibody titer of the immunized mouse was determined by plaque decrease assay. As a result, the mouse immunized with purified WNV-like particles expressed neutralization antibody at a high level (FIG. 9).

Example 6

Establishment of Transformed Cell (1) Establishment of Adherent Transformed Cell Single layer CHO-K1 cells after 7 passages were spread the day before transfection on φ60 mm dish at 1:5, 1:10 or 1:20 split, and the next day, pWPME12 (5 μg) was introduced into 30-40% confluent cells. After culture for 2 days before formation of a single layer, the cells were split at 1:5, 1:10 or 1:20, and cultured in a selection medium containing Blasticidin S (BS) (10 μg/ml) in a φ100 mm dish for 8 days (medium was changed once). 24 colonies grown in the selection medium were taken by a penicillin cup method, transferred to a 24 well plate and further cultured in a selection medium (hereafter selection medium containing BS). Thereafter, the cells were gradually grown by passaging in a 24-well plate, a 6-well plate and a φ100 mm dish, and the obtained cells were cryopreserved. The amount of WNV E protein in the medium cultured in the 24-well plate and 6-well plate was measured according to ELISA, and colony #22 was selected, which showed the maximum production amount. Then, the colony #22 cells were subcloned by a limit dilution method according to a conventional method, and clone #22.6 cells and sub-clone #22.6.6 cells were selected, which showed the maximum WNV E protein production levels according to ELISA. FIG. 10 shows comparison results of expression and secretion of E protein antigen between parent cells and each clone by Western blot.

(2) Acclimation of Adherent Transformed Cell in Serum-Free Medium

The adherent clone #22.6 cells or sub-clone #22.6.6 cells cryopreserved in the above-mentioned (1) were placed back in F12K medium (GIBCO) containing 10 μg/ml BS and 10% FBS, and the growth was confirmed by maintaining for 3-4 passages. F12K medium containing 10 μg/ml BS and 10% FBS and CHO-S-SFM II medium containing 10 μg/ml BS were mixed in the same amount and the cells were cultured in the resulting medium (finally containing 5% FBS) for two passages to initiate acclimation in a serum-free medium. Thereafter, the cells were cultured in a medium containing the same amount of CHO-S-SFM II medium (GIBCO) containing 10 μg/ml BS for two or more passages, and the FBS concentration and ratio of F12K medium were gradually decreased by half.

When the cells were detached from the culture flask by pipetting with PBS (−) even without addition of a trypsin-EDTA solution, they were continuously passaged only in CHO-S-SFM II medium. When the growth of the cells was fine (growth to about $5\text{-}10\times10^5$/ml with viable cells of not less than 95% by passage of $1\text{-}2\times10^5$/ml) and the cells were capable of passage in the medium by pipetting, they were judged to have acclimated in a serum-free medium. The cells were further passaged, and complete acclimation (Full-Adapt) cells that showed growth of $1\times10^6$/ml consecutively for 3 or more times and best acclimation (Best-Adapt) cells that showed growth of not less than $1\times10^6$/ml for 10 consecutive times were cryopreserved (#22.6S and #22.6.6S cells).

In addition, since the adherent CHO cells showed radical property change of becoming non-adherent cells during the acclimation process in a serum-free medium, they had a possibility of decreasing the production amount of antigen protein in this process. Thus, acclimated non-adherent cells #22.6S were cloned and re-cloned. The cloning method followed a conventional method. However, since the growth of the acclimation non-adherent cells showed high dependency on the cell density, the number of cells sown per well was set to 3, 10, 30 and 100. Respective growing clones were preferentially selected from the wells with less number of cells sown, and the production amount of protein was examined by ELISA and IFA. However, there was not found any noticeable difference between the selected plural clones and sub-clones.

INDUSTRIAL APPLICABILITY

The present invention can efficiently secrete and produce VLP of WNV, and can stably supply subunit vaccines of WNV containing the VLP as an active ingredient at a low cost and with safety. In addition, the WNV VLP secretion expression vector of the present invention itself can be used as a DNA vaccine of WNV.

This application is based on a patent application No. 2007-290169 filed in Japan (filing date: Nov. 7, 2007), the contents of which are incorporated in full herein.

SEQUENCE LISTING

```
<160> NUMBER OF SEQ ID NOS: 37

<210> SEQ ID NO 1
<211> LENGTH: 25
<212> TYPE: PRT
<213> ORGANISM: Artificial Sequence
<220> FEATURE:
<223> OTHER INFORMATION: signal peptide

<400> SEQUENCE: 1

Ser Ser Lys Gln Lys Lys Arg Gly Gly Lys Thr Gly Ile Ala Val Met
1               5                   10                  15

Ile Gly Leu Ile Ala Ser Val Gly Ala
            20                  25

<210> SEQ ID NO 2
<211> LENGTH: 501
<212> TYPE: DNA
<213> ORGANISM: West Nile virus
<220> FEATURE:
<221> NAME/KEY: CDS
<222> LOCATION: (1)..(501)

<400> SEQUENCE: 2 gtt acc ctc tct aac ttc caa ggg aag gtg atg atg acg gta aat gct      48
Val Thr Leu Ser Asn Phe Gln Gly Lys Val Met Met Thr Val Asn Ala
1               5                   10                  15 act gac gtc aca gat gtc atc acg att cca aca gct gct gga aag aac      96
Thr Asp Val Thr Asp Val Ile Thr Ile Pro Thr Ala Ala Gly Lys Asn
            20                  25                  30 cta tgc att gtc aga gca atg gat gtg gga tac atg tgc gat gat act     144
Leu Cys Ile Val Arg Ala Met Asp Val Gly Tyr Met Cys Asp Asp Thr
        35                  40                  45 atc act tat gaa tgc cca gtg ctg tcg gct ggt aat gat cca gaa gac     192
Ile Thr Tyr Glu Cys Pro Val Leu Ser Ala Gly Asn Asp Pro Glu Asp
50                  55                  60 atc gac tgt tgg tgc aca aag tca gca gtc tac gtc agg tat gga aga     240
Ile Asp Cys Trp Cys Thr Lys Ser Ala Val Tyr Val Arg Tyr Gly Arg
65                  70                  75                  80 tgc acc aag aca cgc cac tca aga cgc agt cgg agg tca ctg aca gtg     288
Cys Thr Lys Thr Arg His Ser Arg Arg Ser Arg Arg Ser Leu Thr Val
                85                  90                  95 cag aca cac gga gaa agc act cta gcg aac aag aag ggg gct tgg atg     336
Gln Thr His Gly Glu Ser Thr Leu Ala Asn Lys Lys Gly Ala Trp Met
            100                 105                 110 gac agc acc aag gcc aca agg tat ttg gta aaa aca gaa tca tgg atc     384
Asp Ser Thr Lys Ala Thr Arg Tyr Leu Val Lys Thr Glu Ser Trp Ile
        115                 120                 125 ttg agg aac cct gga tat gcc ctg gtg gca gcc gtc att ggt tgg atg     432
Leu Arg Asn Pro Gly Tyr Ala Leu Val Ala Ala Val Ile Gly Trp Met
    130                 135                 140 ctt ggg agc aac acc atg cag aga gtt gtg ttt gtc gtg cta ttg ctt     480
```

```
Leu Gly Ser Asn Thr Met Gln Arg Val Val Phe Val Val Leu Leu Leu
145                 150                 155                 160 ttg gtg gcc cca gct tac agc                                              501
Leu Val Ala Pro Ala Tyr Ser
                165

<210> SEQ ID NO 3
<211> LENGTH: 167
<212> TYPE: PRT
<213> ORGANISM: West Nile virus

<400> SEQUENCE: 3

Val Thr Leu Ser Asn Phe Gln Gly Lys Val Met Met Thr Val Asn Ala
1               5                   10                  15

Thr Asp Val Thr Asp Val Ile Thr Ile Pro Thr Ala Ala Gly Lys Asn
                20                  25                  30

Leu Cys Ile Val Arg Ala Met Asp Val Gly Tyr Met Cys Asp Asp Thr
            35                  40                  45

Ile Thr Tyr Glu Cys Pro Val Leu Ser Ala Gly Asn Asp Pro Glu Asp
        50                  55                  60

Ile Asp Cys Trp Cys Thr Lys Ser Ala Val Tyr Val Arg Tyr Gly Arg
65                  70                  75                  80

Cys Thr Lys Thr Arg His Ser Arg Arg Ser Arg Arg Ser Leu Thr Val
                85                  90                  95

Gln Thr His Gly Glu Ser Thr Leu Ala Asn Lys Lys Gly Ala Trp Met
                100                 105                 110

Asp Ser Thr Lys Ala Thr Arg Tyr Leu Val Lys Thr Glu Ser Trp Ile
            115                 120                 125

Leu Arg Asn Pro Gly Tyr Ala Leu Val Ala Ala Val Ile Gly Trp Met
        130                 135                 140

Leu Gly Ser Asn Thr Met Gln Arg Val Val Phe Val Val Leu Leu Leu
145                 150                 155                 160

Leu Val Ala Pro Ala Tyr Ser
                165

<210> SEQ ID NO 4
<211> LENGTH: 1503
<212> TYPE: DNA
<213> ORGANISM: West Nile virus
<220> FEATURE:
<221> NAME/KEY: CDS
<222> LOCATION: (1)..(1503)

<400> SEQUENCE: 4 ttc aac tgc ctt gga atg agc aac aga gac ttc ttg gaa gga gtg tct         48
Phe Asn Cys Leu Gly Met Ser Asn Arg Asp Phe Leu Glu Gly Val Ser
1               5                   10                  15 gga gca aca tgg gtg gat ttg gtt ctc gaa ggc gac agc tgc gtg act         96
Gly Ala Thr Trp Val Asp Leu Val Leu Glu Gly Asp Ser Cys Val Thr
                20                  25                  30 atc atg tct aag gac aag cct acc atc gat gtg aag atg atg aat atg        144
Ile Met Ser Lys Asp Lys Pro Thr Ile Asp Val Lys Met Met Asn Met
            35                  40                  45 gag gcg gcc aac ctg gca gag gtc cgc agt tat tgc tat ttg gct acc        192
Glu Ala Ala Asn Leu Ala Glu Val Arg Ser Tyr Cys Tyr Leu Ala Thr
        50                  55                  60 gtc agc gat ctc tcc acc aaa gct gcg tgc ccg acc atg gga gaa gct        240
Val Ser Asp Leu Ser Thr Lys Ala Ala Cys Pro Thr Met Gly Glu Ala
65                  70                  75                  80
```

-continued

```
cac aat gac aaa cgt gct gac cca gct ttt gtg tgc aga caa gga gtg      288
His Asn Asp Lys Arg Ala Asp Pro Ala Phe Val Cys Arg Gln Gly Val
             85                  90                  95 gtg gac agg ggc tgg ggc aac ggc tgc gga cta ttt ggc aaa gga agc      336
Val Asp Arg Gly Trp Gly Asn Gly Cys Gly Leu Phe Gly Lys Gly Ser
100                 105                 110 att gac aca tgc gcc aaa ttt gcc tgc tct acc aag gca ata gga aga      384
Ile Asp Thr Cys Ala Lys Phe Ala Cys Ser Thr Lys Ala Ile Gly Arg
            115                 120                 125 acc atc ttg aaa gag aat atc aag tac gaa gtg gcc att ttt gtc cat      432
Thr Ile Leu Lys Glu Asn Ile Lys Tyr Glu Val Ala Ile Phe Val His
        130                 135                 140 gga cca act act gtg gag tcg cac gga aac tac tcc aca cag gtt gga      480
Gly Pro Thr Thr Val Glu Ser His Gly Asn Tyr Ser Thr Gln Val Gly
145                 150                 155                 160 gcc act cag gca ggg aga ttc agc atc act cct gcg gcg cct tca tac      528
Ala Thr Gln Ala Gly Arg Phe Ser Ile Thr Pro Ala Ala Pro Ser Tyr
                165                 170                 175 aca cta aag ctt gga gaa tat gga gag gtg aca gtg gac tgt gaa cca      576
Thr Leu Lys Leu Gly Glu Tyr Gly Glu Val Thr Val Asp Cys Glu Pro
            180                 185                 190 cgg tca ggg att gac acc aat gca tac tac gtg atg act gtt gga aca      624
Arg Ser Gly Ile Asp Thr Asn Ala Tyr Tyr Val Met Thr Val Gly Thr
        195                 200                 205 aag acg ttc ttg gtc cat cgt gag tgg ttc atg gac ctc aac ctc cct      672
Lys Thr Phe Leu Val His Arg Glu Trp Phe Met Asp Leu Asn Leu Pro
    210                 215                 220 tgg agc agt gct gga agt act gtg tgg agg aac aga gag acg tta atg      720
Trp Ser Ser Ala Gly Ser Thr Val Trp Arg Asn Arg Glu Thr Leu Met
225                 230                 235                 240 gag ttt gag gaa cca cac gcc acg aag cag tct gtg ata gca ttg ggc      768
Glu Phe Glu Glu Pro His Ala Thr Lys Gln Ser Val Ile Ala Leu Gly
                245                 250                 255 tca caa gag gga gct ctg cat caa gct ttg gct gga gcc att cct gtg      816
Ser Gln Glu Gly Ala Leu His Gln Ala Leu Ala Gly Ala Ile Pro Val
            260                 265                 270 gaa ttt tca agc aac act gtc aag ttg acg tcg ggt cat ttg aag tgt      864
Glu Phe Ser Ser Asn Thr Val Lys Leu Thr Ser Gly His Leu Lys Cys
        275                 280                 285 aga gtg aag atg gaa aaa ttg cag ttg aag gga aca acc tat ggc gtc      912
Arg Val Lys Met Glu Lys Leu Gln Leu Lys Gly Thr Thr Tyr Gly Val
    290                 295                 300 tgt tca aag gct ttc aag ttt ctt ggg act ccc gca gac aca ggt cac      960
Cys Ser Lys Ala Phe Lys Phe Leu Gly Thr Pro Ala Asp Thr Gly His
305                 310                 315                 320 ggc act gtg gtg ttg gaa ttg cag tac act ggc acg gat gga cct tgc     1008
Gly Thr Val Val Leu Glu Leu Gln Tyr Thr Gly Thr Asp Gly Pro Cys
                325                 330                 335 aaa gtt cct atc tcg tca gtg gct tca ttg aac gac cta acg cca gtg     1056
Lys Val Pro Ile Ser Ser Val Ala Ser Leu Asn Asp Leu Thr Pro Val
            340                 345                 350 ggc aga ttg gtc act gtc aac cct ttt gtt tca gtg gcc acg gcc aac     1104
Gly Arg Leu Val Thr Val Asn Pro Phe Val Ser Val Ala Thr Ala Asn
        355                 360                 365 gct aag gtc ctg att gaa ttg gaa cca ccc ttt gga gac tca tac ata     1152
Ala Lys Val Leu Ile Glu Leu Glu Pro Pro Phe Gly Asp Ser Tyr Ile
    370                 375                 380 gtg gtg ggc aga gga gaa caa cag atc aat cac cat tgg cac aag tct     1200
Val Val Gly Arg Gly Glu Gln Gln Ile Asn His His Trp His Lys Ser
385                 390                 395                 400
```

-continued

```
gga agc agc att ggc aaa gcc ttt aca acc acc ctc aaa gga gcg cag     1248
Gly Ser Ser Ile Gly Lys Ala Phe Thr Thr Thr Leu Lys Gly Ala Gln
            405                 410                 415 aga cta gcc gct cta gga gac aca gct tgg gac ttt gga tca gtt gga     1296
Arg Leu Ala Ala Leu Gly Asp Thr Ala Trp Asp Phe Gly Ser Val Gly
        420                 425                 430 ggg gtg ttc acc tca gtt ggg aag gct gtc cat caa gtg ttc gga gga     1344
Gly Val Phe Thr Ser Val Gly Lys Ala Val His Gln Val Phe Gly Gly
            435                 440                 445 gca ttc cgc tca ctg ttc gga ggc atg tcc tgg ata acg caa gga ttg     1392
Ala Phe Arg Ser Leu Phe Gly Gly Met Ser Trp Ile Thr Gln Gly Leu
        450                 455                 460 ctg ggg gct ctc ctg ttg tgg atg ggc atc aat gct cgt gat agg tcc     1440
Leu Gly Ala Leu Leu Leu Trp Met Gly Ile Asn Ala Arg Asp Arg Ser
465                 470                 475                 480 ata gct ctc acg ttt ctc gca gtt gga gga gtt ctg ctc ttc ctc tcc     1488
Ile Ala Leu Thr Phe Leu Ala Val Gly Gly Val Leu Leu Phe Leu Ser
                485                 490                 495 gtg aac gtg cac gct                                                  1503
Val Asn Val His Ala
        500
```

<210> SEQ ID NO 5
<211> LENGTH: 501
<212> TYPE: PRT
<213> ORGANISM: West Nile virus

<400> SEQUENCE: 5

```
Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220
```

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
            245                 250                 255

Ser Gln Glu Gly Ala Leu His Gln Ala Leu Ala Gly Ala Ile Pro Val
        260                 265                 270

Glu Phe Ser Ser Asn Thr Val Lys Leu Thr Ser Gly His Leu Lys Cys
    275                 280                 285

Arg Val Lys Met Glu Lys Leu Gln Leu Lys Gly Thr Thr Tyr Gly Val
290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
                340                 345                 350

Gly Arg Leu Val Thr Val Asn Pro Phe Val Ser Val Ala Thr Ala Asn
            355                 360                 365

Ala Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
                405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
            435                 440                 445

Ala Phe Arg Ser Leu Phe Gly Gly Met Ser Trp Ile Thr Gln Gly Leu
        450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
                485                 490                 495

Val Asn Val His Ala
            500

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
aaaaaagatc tcgatgtcta agaaaccagg aggg                              34

<210> SEQ ID NO 7
<211> LENGTH: 37
<212> TYPE: DNA
<213> ORGANISM: Artificial Sequence
<220> FEATURE:
<223> OTHER INFORMATION: primer

<400> SEQUENCE: 7
aaaaactcga gcaaaagagt gttcagctcg tccttca                           37

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
agtgctggta ccatgcggag ctcaaaacaa aagaaaaga                    39

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
gctatcggta ccatgagctc aaaacaaaag aaaagagga                    39

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
atcaatggta ccatgtcaaa acaaaagaaa agagga                       36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
aatcggggta ccatgaaaca aagaaaaga ggagga                        36

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
cggcggggta ccatgcaaaa gaaaagagga ggaaag                       36

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
cggagcggta ccatgaagaa aagaggagga aagaccgga                    39

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
agctcaggta ccatgaaaag aggaggaaag accggaatt                                    39

<210> SEQ ID NO 15
<211> LENGTH: 39
<212> TYPE: DNA
<213> ORGANISM: Artificial Sequence
<220> FEATURE:
<223> OTHER INFORMATION: primer

<400> SEQUENCE: 15 tcaaaggta ccatgagagg aggaaagacc ggaattgca                                     39

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
aaacaaggta ccatgggagg aaagaccgga attgcagtca                                   40

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
caaaagggta ccatgggaaa gaccggaatt gcagtc                                       36

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
aagaaaggta ccatgaagac cggaattgca gtcatg                                       36

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
aaaagaggta ccatgaccgg aattgcagtc atgattggc                                    39

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
acagctggta ccatgaacct atgcattgtc agagcaat                                     38

<210> SEQ ID NO 21
<211> LENGTH: 39

```
<212> TYPE: DNA
<213> ORGANISM: Artificial Sequence
<220> FEATURE:
<223> OTHER INFORMATION: primer

<400> SEQUENCE: 21
tgttggggta ccatgtcagc agtctacgtc aggtatgga                              39

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
ggcacactcg agttaagcgt gcacgttcac ggagaggaa                              39

<210> SEQ ID NO 23
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 23

Met Arg Ser Ser Lys Gln Lys Lys Arg Gly Gly Lys Thr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 24

Met Ser Ser Lys Gln Lys Lys Arg Gly Gly Lys Thr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synhetic Sequence

<400> SEQUENCE: 25

Met Ser Lys Gln Lys Lys Arg Gly Gly Lys Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 26

Met Lys Gln Lys Lys Arg Gly Gly Lys Thr
1               5                   10

<210> SEQ ID NO 27
<211> LENGTH: 9
<212> TYPE: PRT
<213> ORGANISM: Artificial Sequence
<220> FEATURE:
```

<223> OTHER INFORMATION: Synthetic Sequence

<400> SEQUENCE: 27

Met Gln Lys Lys Arg Gly Gly Lys Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 28

Met Lys Lys Arg Gly Gly Lys Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 29

Met Lys Arg Gly Gly Lys Thr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 30

Met Arg Gly Gly Lys Thr
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 31

Met Gly Gly Lys Thr
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 32

Met Gly Lys Thr
1

<210> SEQ ID NO 33
<211> LENGTH: 8
<212> TYPE: PRT
<213> ORGANISM: Artificial Sequence
<220> FEATURE:
<223> OTHER INFORMATION: Synthetic Sequence

```
<400> SEQUENCE: 33

Met Ala Lys Arg Gly Gly Lys Thr
1               5

<210> SEQ ID NO 34
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 34

Met Ala Arg Ser Ser Lys Gln Lys Lys Arg Gly Gly Lys Thr
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Artificial Sequence

<400> SEQUENCE: 35

Met Gly Gly Lys Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 36

Met Lys Arg Gly Gly Lys Thr
1               5

<210> SEQ ID NO 37
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 37

Met Arg Ser Ser Lys Gln Lys Lys Arg Gly Gly Lys Thr
1               5                   10
```

The invention claimed is:

1. An isolated signal peptide consisting of amino acid residues 10-25 of the amino acid sequence of SEQ ID NO: 1.

* * * * *